(12) United States Patent
Matsuyama et al.

(10) Patent No.: US 7,591,999 B2
(45) Date of Patent: Sep. 22, 2009

(54) POWDERY PREPARATION FOR NASAL ADMINISTRATION

(75) Inventors: Takahiro Matsuyama, Osaka (JP); Hiroyuki Yoshino, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 162 days.

(21) Appl. No.: 10/547,340

(22) PCT Filed: Mar. 4, 2004

(86) PCT No.: PCT/JP2004/002765

§ 371 (c)(1),
(2), (4) Date: Sep. 1, 2005

(87) PCT Pub. No.: WO2004/078211

PCT Pub. Date: Sep. 16, 2004

(65) Prior Publication Data

US 2006/0204448 A1     Sep. 14, 2006

(30) Foreign Application Priority Data

Mar. 4, 2003  (JP) ............................. 2003-057624
Dec. 24, 2003  (JP) ............................. 2003-427536

(51) Int. Cl.
*A61K 9/14*     (2006.01)
*A61K 9/50*     (2006.01)
*A61K 38/00*   (2006.01)

(52) U.S. Cl. ...................... 424/46; 424/434; 424/489; 424/499; 514/2; 514/951

(58) Field of Classification Search .................. 424/46, 424/434, 489, 499; 514/2, 951
See application file for complete search history.

(56) References Cited

U.S. PATENT DOCUMENTS

| 5,603,943 | A | 2/1997 | Yanagawa |
| 5,626,871 | A | 5/1997 | Makino et al. |
| 5,690,954 | A | 11/1997 | Illum |
| 5,863,554 | A | 1/1999 | Illum |
| 6,197,328 | B1* | 3/2001 | Yanagawa .................. 424/434 |
| 6,458,338 | B1 | 10/2002 | Adjei et al. |
| 6,464,959 | B1 | 10/2002 | Cutie et al. |
| 6,544,497 | B2* | 4/2003 | Zhu et al. ..................... 424/45 |
| 7,166,575 | B2* | 1/2007 | Quay .......................... 514/12 |
| 2002/0006933 | A1* | 1/2002 | Gupta et al. ................ 514/295 |
| 2002/0009789 | A1 | 1/2002 | Hanyu et al. |
| 2002/0058624 | A1 | 5/2002 | Hanyu et al. |
| 2002/0110528 | A1 | 8/2002 | Zhu et al. |
| 2002/0119104 | A1 | 8/2002 | Etter et al. |
| 2003/0031730 | A1 | 2/2003 | Salman |
| 2003/0035774 | A1 | 2/2003 | Adjei et al. |
| 2003/0130203 | A1 | 7/2003 | Christoph et al. |

FOREIGN PATENT DOCUMENTS

| EP | 0 115 627 A1 | 8/1984 |
| JP | 59-130820 A | 7/1984 |
| JP | 62-42888 B2 | 9/1987 |
| JP | 63-115821 A | 5/1988 |
| JP | 63-115822 A | 5/1988 |
| JP | 2-503915 A | 11/1990 |
| JP | 8-27031 A | 1/1996 |
| JP | 11-322582 A | 11/1999 |
| JP | 2002-128704 A | 5/2002 |
| JP | 2002/187852 A | 7/2002 |
| WO | WO-93/25193 A1 | 12/1993 |
| WO | WO 9732596 * | 9/1997 |
| WO | WO-99/24058 A2 | 5/1999 |
| WO | WO-00/12063 A1 | 3/2000 |
| WO | WO-01/82868 A2 | 11/2001 |
| WO | WO-01/82873 A2 | 11/2001 |
| WO | WO-01/82980 A1 | 11/2001 |
| WO | WO-01/91732 A2 | 12/2001 |
| WO | WO-02/05784 A1 | 1/2002 |
| WO | WO-02/05785 A1 | 1/2002 |
| WO | WO-02/41837 A2 | 5/2002 |
| WO | WO-02/066011 A1 | 8/2002 |
| WO | WO-03/007867 A2 | 1/2003 |
| WO | WO-03/015746 A1 | 2/2003 |
| WO | WO-03/026699 A1 | 4/2003 |

OTHER PUBLICATIONS

The Pharmaceutical Society of Japan, Summary of the 27th Preparation Seminar, pp. 19-20, 2002.
O'Hagan et al., Pharmaceutical Research, vol. 7, No. 7, 1990, pp. 772-776.

\* cited by examiner

*Primary Examiner*—Mina Haghighatian
(74) *Attorney, Agent, or Firm*—Birch, Stewart, Kolasch & Birch, LLP

(57) ABSTRACT

According to the present invention, a powdery preparation for nasal administration comprising a physiologically active substance, a non-water-absorbing and hardly water-soluble powder(s) and one or two selected from the group consisting of a mucolytic agent and a nonionic surfactant is provided.

17 Claims, 8 Drawing Sheets

US 7,591,999 B2

POWDERY PREPARATION FOR NASAL ADMINISTRATION

TECHNICAL FIELD

The present invention relates to a powdery preparation for nasal administration, and to a powdery preparation for nasal administration which comprises a physiologically active substance, a non-water-absorbing and hardly water-soluble powder(s), and one or two selected from the group consisting of a mucolytic agent(s) and a nonionic surfactant(s), in which absorption of the physiologically active substance at a nasal mucous membrane is improved.

BACKGROUND ART

Physiologically active peptides such as hormone, cytokine, etc. have an important role in a living body, and it has frequently been carried out to use a physiologically active peptide itself as a medicine manufactured by mass production, or to use a physiologically active peptide as a medicine by structurally changing and modifying it by means of genetic engineering or protein synthesis.

However, the physiologically active peptide involves a risk that it is decomposed by digestive juices or enzymes in digestive tract or at the wall of the digestive tract when it is administered orally. Also, even when it is absorbed by the digestive tract, after the absorption, it circulates in the whole body after passing firstly through liver, so that there are problems that there is a possibility that it is decomposed in the liver (first-pass effect by the liver), and the physiologically active peptide with high hydrophilicity is a polymer and has high polarity whereby it is generally scarcely absorbed by a mucous membrane of the digestive tract.

Thus, to attain sufficient medicinal effects of the physiologically active peptide, it is not generally administered orally but is introduced in the form of injection subcutaneously, intramuscularly or directly into blood circulation. However, administration by an injection requires a patient's attendance at a hospital and is painful, so that the administration at home or without pain is desired.

As one of the administration form, it has been proposed to carry out nasal administration which is to administer a medicine to nasal mucous membrane (particularly, mucous membranes of concha nasalis superior, concha nasalis media, concha nasalis inferior) where epidermis cells having cilia covered by mucus, and basement membrane, and vascular system is developed at the bottom portion. However, the epidermis cells are closely bound by conjugant so that permeability of the physiologically active peptide having a large molecular weight, etc. is low and various preparations have been proposed to improve permeability.

For example, in Japanese Patent Publication No. Sho. 62-42888, there is described a composition for powdery preparation for nasal administration comprising physiologically active polypeptides and an agent (crystalline cellulose, etc.) which is water-absorbing and hardly water-soluble, and in Japanese Unexamined Patent Publication No. Hei. 8-27031, there is disclosed a composition for nasal absorption in which a physiologically active substance having a molecular weight of 40000 or less is uniformly dispersed, attached and bound to powdery or crystalline polyvalent metal compound carrier (aluminum compound, calcium compound, etc.) having an average particle diameter of 250 µm or less.

In summary collection of 27th Formulation Seminar of The Pharmaceutical Society of Japan, pp. 19-20, there has been reported that improvement in bioavailability through nasal administration had been observed when a hardly soluble powder such as calcium carbonate, ethyl cellulose, talc, barium sulfate, etc. had been used as a pharmaceutical carrier with regard to a water-soluble compound having a molecular weight of 1000 or more.

Also, in Japanese Unexamined Patent Publication No. Hei. 11-322582, a composition for nasal administration in which a medicine is uniformly dispersed and adsorbed on a primary granulated carrier of microcrystalline, etc. (calcium carbonate powder, etc.) having a number of cavities on the surface thereof has been disclosed.

Moreover, in Japanese Unexamined Patent Publication No. 2002-128704, there is described a nasal administration type preparation comprising a physiologically active substance, a carrier and an absorption promoter in living body (highly substituted hydroxypropyl cellulose, micro-crystalline cellulose), and as the carrier, a water-soluble polymer compound (cellulose derivatives such as crystalline cellulose, methyl cellulose, ethyl cellulose, carboxymethyl cellulose, etc.) has been mentioned.

Also, in Japanese Unexamined Patent Publication No. Sho. 59-130820, an aqueous solution for nasal administration has been disclosed in which Polysorbate 80 which is a nonionic surfactant is added to calcitonin together with acetic acid and sodium acetate, and they are dissolved in purified water.

In Pharmaceutical Research, vol. 7, No. 7, pp. 772-776 (1990), there has been reported that when N-acetyl-L-cysteine, etc. are added with high concentrations to an aqueous buffer containing human growth hormone, and the preparation is nasally administered to rats, bioavailability is slightly improved.

However, these preparations for nasal administration have the problem that improvement in absorption is not sufficient.

DISCLOSURE OF THE INVENTION

The present invention is to provide a powdery preparation for nasal administration which comprises a physiologically active substance, a non-water-absorbing and hardly water-soluble powder(s), and one or two selected from the group consisting of a mucolytic agent(s) and a nonionic surfactant(s), and by the nasal administration, a sufficient concentration in blood stream for the activity of the physiologically active substance in a living body can be accomplished.

The present inventors have found that a non-water-absorbing and hardly water-soluble powder(s) and at least one selected from the group consisting of a mucolytic agent(s) and a nonionic surfactant(s) are added to the physiologically active substance, and the resulting product is administered nasally, then, the nasal absorption of the physiologically active substance can be markedly improved whereby the present invention has been accomplished.

That is, the present invention relates to a powdery preparation for nasal administration which comprises a physiologically active substance, a non-water-absorbing and hardly water-soluble powder(s), and one or two selected from a mucolytic agent(s) and a nonionic surfactant(s).

When the powdery preparation for nasal administration of the present invention is sprayed/inhaled into nasal cavity, due to the presence of the non-water-absorbing and hardly water-soluble powder(s), the physiologically active substance and the mucolytic agent and/or the nonionic surfactant are attached to mucous membrane of the nasal cavity and retained, and yet the non-water-absorbing and hardly water-soluble powder(s) does/do not absorb mucus of the nasal mucous membrane, so that the physiologically active substance and the mucolytic agent- and/or the nonionic surfactant are dissolved in a minute amount of the mucus, whereby the physiologically active substance and the mucolytic agent- and/or the nonionic surfactant cause locally high concentration solution. In such a state, by utilizing concentration gradient of the physiologically active substance, and according to the action of the mucolytic agent- and/or the nonionic surfactant dissolved at a high concentration, absorption property itself through the nasal mucous membrane is locally improved and the physiologically active substance can reach from the nasal mucous membrane the blood vessel system existing under the membrane with good efficiency, whereby nasal absorption of the physiologically active substance can be promoted.

Also, a non-water-absorbing and hardly water-soluble powder(s) does/do not itself absorb a medicine dissolved in the nasal cavity, so that an availability of the medicine for absorption is not lowered.

And yet, the powdery preparation for nasal administration of the present invention acts on the nasal mucous membrane locally and scatteringly, so that it does not act on the whole nasal mucous membrane as in the liquid preparation for nasal administration, whereby it causes less adverse effects on the nasal mucous membrane.

BEST MODE FOR CARRYING OUT THE INVENTION

Figure 1:
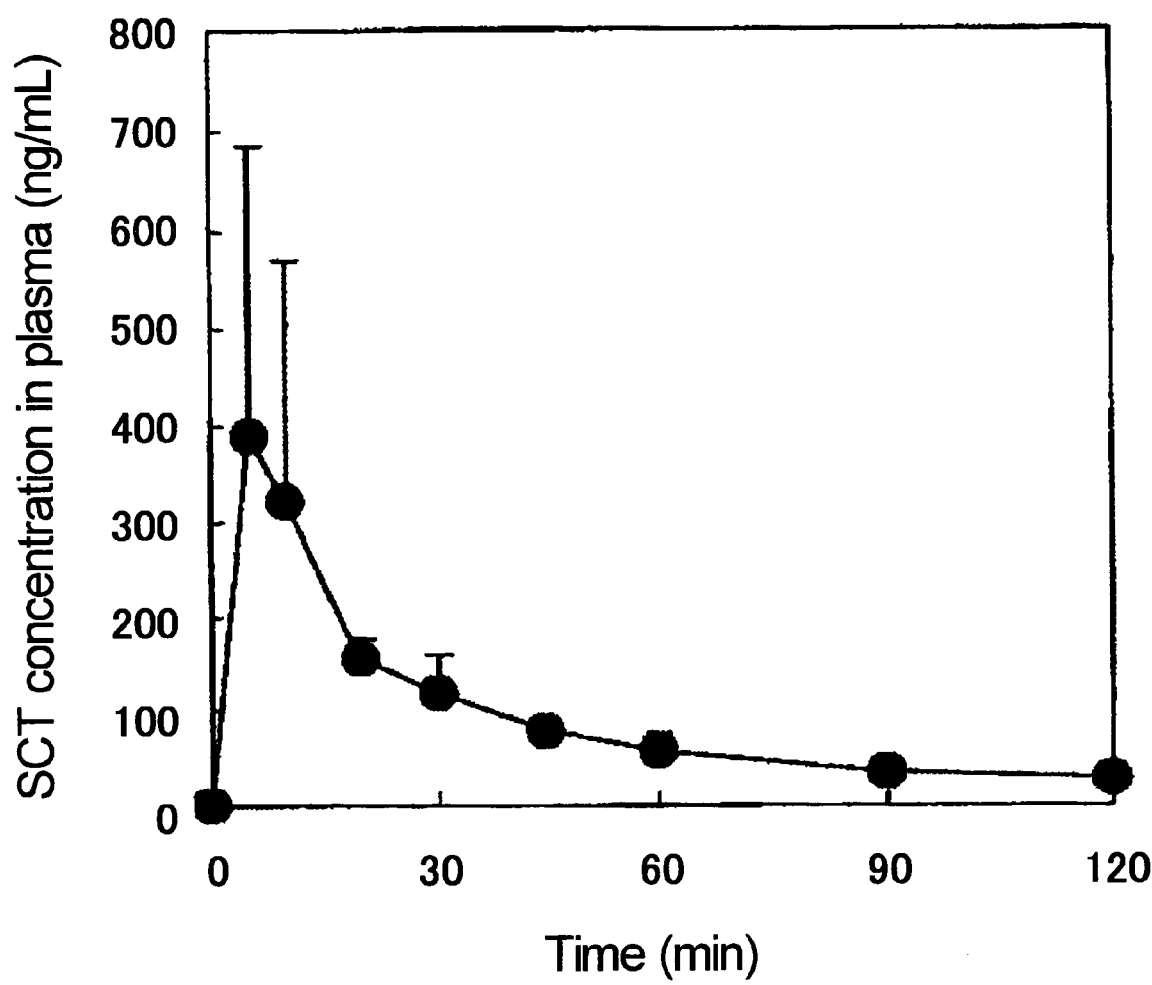
FIG. 1 shows plasma salmon calcitonin (hereinafter referred to as SCT) concentration versus time profile when a powder for administration containing SCT, N-acetyl-L-cysteine (hereinafter referred to as NAC) and ethyl cellulose (hereinafter referred to as EC) is nasally administered to rats.

In the non-water-absorbing and hardly water-soluble powder(s) to be used for the powdery preparation for nasal administration of the present invention, as a non-water-absorbing and hardly water-soluble substance, there may be mentioned a substance preferably having a water absorption rate of 5 mm/min or less, and a solubility in water (25° C., hereinafter the same) of 100 mg/L or less, more preferably a substance having a water absorption rate of 1 mm/min or less, and a solubility in water of 50 mg/L or less, most preferably a substance having a water absorption rate of 0.5 mm/min or less, and a solubility in water of 20 mg/L or less.

The water absorption rate means a value in which, according to the method described in summary collection of 16th Symposium on Particulate Preparations and Designs (1999), pp. 163 to 167, powder is filled in a glass tube having an inner diameter of 2.1 cm, while the glass tube is maintained at a vertical state and a bottom end thereof is dipped in pure water, a distance from the bottom end of the glass tube to the upper end of water absorbed upward from the bottom end of the glass tube is measured.

Also, the powdery preparation for nasal administration of the present invention is to be administered by spraying into nasal cavity using a gas, so that it is in a powdery form as a whole, preferably containing a solvent such as water, etc. as little as possible.

Specific examples of the non-water-absorbing and hardly water-soluble substances may include various kinds of materials such as non-water-absorbing and hardly water-soluble cellulose derivatives (for example, ethyl cellulose, cellulose acetate, nitro cellulose, cellulose triacetate, cellulose acetate phthalate, hydroxypropyl-methyl cellulose phthalate, hydroxypropylmethyl cellulose acetate succinate, carboxymethylethyl cellulose, etc.), non-water-absorbing and hardly water-soluble higher fatty acid and its ester or salt (hardened oil, hydrogenated soybean oil, carnauba wax, bleached beeswax, sucrose fatty acid ester, stearic acid, a salt of stearic acid, etc.), non-water-absorbing and hardly water-soluble biodegradable polymers (polylactic acid, polyglycolic acid, lactic acid-glycolic acid copolymer, etc.), non-water-absorbing and hardly water-soluble synthetic polymers (polyethylene terephthalate, polyethylene, polyvinyl chloride, etc.), non-water-absorbing and hardly water-soluble polyvalent metal salt (calcium carbonate, barium sulfate, hydroxy-apatite, etc.), non-water-absorbing and hardly water-soluble metal oxides (talc, silicon dioxide, titanium oxide, etc.), and the non-water-absorbing and hardly water-soluble cellulose derivatives are preferably used, in particular, ethyl cellulose and/or cellulose acetate is/are preferably used, and from the view point of non-water-absorbing property, ethyl cellulose and/or cellulose acetate of a high substitution degree is/are particularly preferred.

Here, the high substitution degree means that among the hydroxyl groups of L-glucose constituting the cellulose molecule, hydrogen atoms of the hydroxyl groups which are not used for bonds between L-glucoses are substituted by a substituent(s) on an average of 70% or more, preferably on an average of 80% or more, particularly preferably on an average of 85% or more.

Also, as the non-water-absorbing and hardly water-soluble powder(s), it is preferred that mucus of the nasal mucous membrane, etc. are hardly attached to the surface of the powder particles, so that the powder particles having no cavity on their surface are preferred. Though an average diameter of the powder particles may vary depending on the kinds of the physiologically active substance, and the mucolytic agent- and/or the nonionic surfactant to be contained in the powdery preparation for nasal administration, form of use, etc., it may be usually in the range of 5 to 200 μm, preferably in the range of 20 to 150 μm, more preferably in the range of 30 to 120 μm, most preferably in the range of 40 to 100 μm.

Though the non-water-absorbing and hardly water-soluble powder(s) may be those which are commercially available powder product(s) as such, the non-water-absorbing and hardly water-soluble solid substance may be processed or the commercially available powder product may be further processed to prepare a desired particle diameter and shape and the processed product is used.

Also, the non-water-absorbing and hardly water-soluble powder(s) may be one non-water-absorbing and hardly water-soluble powder, or a plural number of non-water-absorbing and hardly water-soluble powders.

As a method of processing the non-water-absorbing and hardly water-soluble substance, any conventional fine particle-formation method can be optionally used and there may be employed, for example, a physically pulverizing method such as jet-mill pulverization, hummer mill pulverization, rotary type ball mill pulverization, vibration ball mill pulverization, beads mill pulverization, shaker mill pulverization, rod mill pulverization, tube mill pulverization, etc.; a crystallization method in which the non-water-absorbing and hardly water-soluble substance is once dissolved in a solvent, then crystallized by changing temperature, changing a composition of the solvents, etc., and recovering by the method of centrifugation or filtration, etc.; a spray drying method in which the non-water-absorbing and hardly water-soluble substance is once dissolved in a solvent, and spraying the solution into a drying room of a spray dryer using a spray nozzle to volatilize the solvent in the sprayed solution within a short period of time, and the like.

Also, the non-water-absorbing and hardly water-soluble powder(s) may be subjected to a treatment so that the particle diameter falls within a predetermined range by suppressing the fluctuation of the particle diameter by means of the method such as sieving, fractioning due to sedimentation by gravity, fractioning by centrifugation, fractioning by inertia force due to gas flow, etc.

One or two selected from the group consisting of a mucolytic agent(s) and a nonionic surfactant(s) mean either of (a) a mucolytic agent(s), (b) a nonionic surfactant(s) or (c) a mucolytic agent(s) and a nonionic surfactant(s), and in either of (a) to (c), the mucolytic agent(s), and the nonionic surfactant(s) may comprise only one component or may comprise a plural number of components.

Though as the mucolytic agent- and/or the nonionic surfactant, any material which can promote absorption of the physiologically active substance to the mucous membrane may be used, a material which has less adverse effects on the nasal mucous membrane such as stimulating property, etc., and which can markedly improve absorption from the nasal mucous membrane in a small amount may be preferably used. The mucolytic agent alone, or a combination of the mucolytic agent and the nonionic surfactant are preferably used, and in view of stimulating property to the nasal mucous membrane, the mucolytic agent is most preferably used.

As preferred examples of the mucolytic agents, there may be mentioned cysteine derivatives, and active SH group-containing alcohols. As the cysteine derivatives, there may be mentioned, for example, N-($C_{2-5}$ alkanoyl)cysteine such as N-acetylcysteine, etc., S-($C_{1-4}$ alkyl)cysteine such as S-methylcysteine, S-ethylcysteine, etc., and S-($C_{2-5}$ carboxyalkyl) cysteine such as S-carboxymethylcysteine, etc.

Also, as the cysteine derivatives, cysteine-containing peptides are included, and there may be mentioned, for example, glutathiones which are a kind of tripeptides. Examples of the glutathiones may include, in addition to glutathione, glutathione esters such as a glutathione $C_{1-8}$ alkyl ester (see U.S. Pat. No. 4,784,685), etc.

As the cysteine of these cysteine derivatives, DL-form, L-form and D-form are included, and in particular, L-cysteine is preferred.

As the active SH group-containing alcohol, there may be mentioned a $C_{3-6}$ active SH group-containing alcohol, more specifically 1,4-dithiothreitol.

As the nonionic surfactant, a nonionic surfactant which has low protein-denaturing ability and has low membrane solubilizing property is preferred.

As such a nonionic surfactant may be mentioned a polyoxyethylene-$C_{10-14}$ alkyl ether, a polyoxyethylene-($C_{6-10}$ alkyl-phenyl) ether, a $C_{6-10}$ alkyl-glucose ether and an N-($C_{6-10}$ alkyl)carbamoyl-$C_{1-4}$ alkyl-glucose ether, etc.

As the polyoxyethylene-$C_{10-14}$ alkyl ether and the polyoxyethylene-($C_{6-10}$ alkyl-phenyl) ether, those having a polyoxyethylene portion in the range of 65 to 90% by weight based on the whole molecule are preferred, and there may be specifically mentioned polyoxyethylene-lauryl ether having an average molecular weight of 560 to 1300 [for example, BL-9 available from Nikkol: polyoxyethylene(9) lauryl ether; BL-25: polyoxyethylene(25) lauryl ether]; polyoxy-ethylene-octylphenyl ether having an average molecular weight of 600 to 800, particularly polyoxyethylene-tert-octylphenyl ether having an average molecular weight of 600 to 800 [for example, Triton X-100 available from Nacalai: polyoxyethylene (9-10) p-tert-octylphenyl ether, Triton X-102: polyoxyethylene (12-13) p-tert-octylphenyl ether]; polyoxyethylene-nonylphenyl ether having an average molecular weight of 600 to 700, particularly polyoxyethylene-n-nonylphenyl ether having an average molecular weight of 600 to 700 [for example, NP-10 available from Nikkol: polyoxyethylene (10) p-n-nonylphenyl ether].

As the $C_{6-10}$ alkyl-glucose ether and N-($C_{6-10}$ alkyl)-carbamoyl-$C_{1-4}$ alkyl-glucose ether, those having a glucose portion in the range of 50 to 65% by weight based on the whole molecule is preferred, and there may be specifically mentioned 1-O-octyl-β-D-glucopyranoside, particularly 1-O-n-octyl-β-D-glucopyranoside; 6-O-(N-heptylcarbamoyl)methyl-α-D-glucopyranoside, particularly 6-O-(N-n-heptylcarbamoyl)methyl-α-D-glucopyranoside.

Moreover, as the nonionic surfactant, a nonionic surfactant whose concentration in an aqueous solution at which 50% of red blood cells are hemolysed is 1% by weight or more, particularly 5% by weight or more, is preferred since it causes less adverse effects on the nasal mucous membrane.

Here, the concentration of the nonionic surfactant in an aqueous solution at which 50% of red blood cells are hemolysed can be estimated by the following method. Red blood cells are added in a ratio of 0.2% by weight to physiological salines containing the nonionic surfactant which had been adjusted to various concentrations, the mixtures are allowed to stand at 37° C. for 10 minutes, and the absorbance (540 nm) of hemoglobin in the supernatant is measured. On the other hand, when red blood cells are added to purified water with the same ratio and are completely hemolysed, the absorbance is considered to be 100%. Hemolysis ratios of the red blood cells at the respective concentrations of the nonionic surfactant are calculated, whereby the concentration of the nonionic surfactant at which the hemolysis ratio becomes 50% is estimated by an interpolation method.

As the physiologically active substance, it is not particularly limited so long as it is a medicine having less stimulation to nasal mucous membrane, but a physiologically active substance which shows medicinal effect with a small dose is preferred since a large amount of medicine cannot be administered by nasal administration.

Also, when the powdery preparation for nasal administration of the present invention is applied to a physiologically active substance which can be hardly absorbed by nasal route, improvement in nasal absorption of the physiologically active substance becomes remarkable, so that a hydrophilic hardly-absorbable substance is preferably used as the physiologically active substance.

Incidentally, the term hardly-absorbable means that when an aqueous solution of a physiologically active substance is nasally administered to human by spraying, 5% or less of the sprayed amount is absorbed.

As such a physiologically active substance may be mentioned those used as antibiotics, blood-forming agents, infectious diseases treating agents, anti-dementia, antiviral agents, anti-tumor agent, antipyretic agents, analgesic, anti-inflammatory, antiulcer, antiallergic agent, antipsychotic medicine, cardiotonic agent, cardiac dysrhythmia treating agent, vasodilators, hypotensive agent, diabetes treating agent, anticoagulant, cholesterol lowering agent, osteoporosis treating agent, hormone agent, vaccine, etc.

As these substances, in addition to the low molecular weight physiologically active substance, peptidic physiologically active substance, polysaccharide physiologically active substance, etc. are included, and the powdery preparation for nasal administration of the present invention shows marked effects when it is applied to the peptidic physiologically active substance and/or polysaccharide physiologically active substance, and it is particularly preferably applied to the peptidic physiologically active substance.

As the peptidic physiologically active substances, there may be mentioned an antagonist, agonist or soluble receptors thereof and derivatives thereof, and with regard to a substance having sugar chain, those which have a different structure in chain are also included. If necessary, these substances may be modified by a synthetic polymer such as polyethylene glycol, etc., or a natural polymer such as hyaluronic acid, etc., or else, may be modified by an optional sugar such as galactose, mannose, etc., or may be modified by a sugar chain or non-peptidic compound. Also, they may be a substance which provides a lipid-soluble property to the peptidic physiologically active substance, such as phospholipids, fatty acids, etc. These peptidic physiologically active substances have a molecular weight of 200 to 200000, preferably have a molecular weight of 200 to 50000, more preferably have a molecular weight of 200 to 25000, and most preferably have a molecular weight of 200 to 10000.

Preferred peptidic physiologically active substances may include cytokine, peptide hormone, growth factor, a factor which acts on cardiac vessel system, a factor which acts on central and peripheral nerve systems, etc., and specific examples are as mentioned below.

As the cytokine, there may be mentioned interferons (for example, interferon-α, -β, -γ), interleukins (for example, interleukin-1 to 11), tumor necrosis factor (for example, TNF-α, -β), leukemia inhibitory factor (LIF), blood-forming factor [for example, erythropoietin, thrombopoietin, granulocyte colony stimulating factor (G-CSF), granulocyte-macrophage colony stimulating factor (GM-CSF), macrophage colony stimulating factor (M-CSF)], etc.

As the peptide hormone, there may be mentioned insulin, growth hormone, gonadotropic hormone, melanocyto-stimulating hormone, luteotropic hormone, luteinizing hormone, luteinizing hormone-releasing hormone (LH-RH) and its derivatives (goserelin, buserelin, leuprorelin), adrenocorticotropic hormone (ACTH), parathyroid hormone (PTH), thyroid-stimulating hormone (TSH), thyrotropin-releasing hormone (TRH) and its derivatives (taltirelin), calcitonin, etc.

As the growth factor, there may be mentioned nerve growth factors (for example, NGF, NGF-2/NT-3), epidermal growth factor (EGF), fibroblast growth factor (FGF), insulin-like growth factor (IGF), transforming growth factor (TGF), platelet-derived growth factor (PDGF), hepatocytes growth factor (HGF), etc.

As the factor which acts on cardiac vessel system, there may be mentioned endothelin, endothelin inhibitor, endothelin antagonist, endothelin formation enzyme inhibitor, desmopressin, renin, angiotensin I to III, atrial natriumuretic peptide (ANP), etc.

As the factor which acts on central and peripheral nerve systems, there may be mentioned enkephalin, endorphin, dynorphin, neoendorphin, etc.

In these peptidic physiologically active substances, a soluble receptor of the polypeptide is included in the concept. In these peptidic physiologically active substance, those which are chemically modified by a polymer such as polyethylene glycol, or by a natural polymer such as chondroitin, polysaccharides, or by a non-peptidic substance may be respectively included. The non-peptidic substance herein mentioned may be a ligand to a receptor, or an antigen to an antibody. Moreover, the above-mentioned peptidic physiologically active substance may include those in which a plural number of peptides are bound by a chemical method or a genetic recombinant technique.

As the physiologically active polysaccharide substance, there may be mentioned a low molecular weight heparin, a heparin-like substance, etc.

Also, in the powdery preparation for nasal administration of the present invention, the physiologically active substance can be taken into a body from a blood vessel system under the mucous membrane of the nasal cavity immediately after administration, and a time interval from the administration to the generation of the medicinal effects is short. Therefore, it can also be suitably employed for a physiologically active substance with which a short onset time (a time interval between the administration of a medicine and the generation of the medicinal effects) produces therapeutic advantages.

Thus, the powdery preparation for nasal administration of the present invention can be suitably applied to a physiologically active substance, for example, narcotic analgesic (for example, alkaloid type narcotic), migraine treating agent [for example, 5-hydroxytryptamine (HT) 1 receptor agonist, neurokinin (NK) 1 receptor antagonist, iGluR5 receptor antagonist, β adrenergic blocking agent], preventive for travel sickness [for example, central anti-cholinergic agent, antihistaminic agent, 5-hydroxytryptamine (HT) 1 receptor agonist], antiemetic [for example, neurokinin (NK) 1 receptor antagonist, 5-hydroxytryptamine (HT) 3 receptor antagonist], sexual function improving agent [for example, phosphodiesterase (PDE) 5 inhibitor, α-melanin cell stimulating hormone (MSH) analogue, dopamine D2 receptor agonist, non-steroidal androgen receptor modulator], diabetes treating agent (for example, insulin), first aid medicine at the time of low blood sugar (for example, glucagon), etc.

Though a formulation ratio of the powdery preparation for nasal administration of the present invention may vary depending on various factors such as a kind of the physiologically active substance, kinds of the mucolytic agent- and/or the nonionic surfactant, used form thereof, etc., the physiologically active substance may be used in an amount of 0.1 to 80% by weight based on the whole preparation, the non-water-absorbing and hardly water-soluble powder(s) may be used in the amount of 15 to 99.4% by weight based on the same, and the mucolytic agent- and/or the nonionic surfactant may be used in the amount of 0.5 to 5% by weight based on the same.

A (spraying/inhalation) dose of the powdery preparation for nasal administration of the present invention is generally 3 to 50 mg/ time, preferably 5 to 20 mg/each time. Even in such a small amount of (spraying/inhalation) dose, the powdery preparation for nasal administration of the present invention can give an excellent nasal absorption promoting effect by using a small amount of the non-water-absorbing and hardly water-soluble powder(s), and the mucolytic agent- and/or the nonionic surfactant. Thus, a physiologically active substance which is required to be absorbed in a living body at a relatively large dose (1 mg/person/time or so) for generating a physiological activity can be nasally absorbed.

Also, the non-water-absorbing and hardly water-soluble powder(s) does/do not itself show any physiological activity at the nasal mucous membrane, so that when a physiologically active substance which shows sufficient physiological activity with a small (spraying/inhalation) dose is to be nasally administered, an amount of the non-water-absorbing and hardly water-soluble powder(s) may be intentionally increased to control fluctuation of a dose of the physiologically active substance to be administered per one spraying/inhalation.

The physiologically active substance, and the mucolytic agent- and/or the nonionic surfactant to be contained in the powdery preparation for nasal administration of the present invention can be mixed in a powder state with the non-water-absorbing and hardly water-soluble powder(s) to give the powdery preparation for nasal administration of the present invention, and the preparation can be used as such. However, in this case, it is preferred to regulate a density and particle diameter of the powder particles in order to prevent the respective components from separation at the time of administration into nasal cavity by spraying/inhalation.

For example, it is preferred that densities calculated from the outer shape of the physiologically active substance, and the mucolytic agent- and/or the nonionic surfactant are in the range of 0.7 to 1.5-fold to the density calculated from the outer shape of the non-water-absorbing and hardly water-soluble powder(s), preferably in the range of 0.8 to 1.3-fold, and the particle diameters of the powder of the physiologically active substance, and the mucolytic agent- and/or the nonionic surfactant are in the range of 0.3 to 1.2-fold to the particle diameter of the non-water-absorbing and hardly water-soluble powder(s), preferably in the range of 0.4 to 1.1-fold.

Preparation of powder and designing of the particle diameter of the physiologically active substance, and the mucolytic agent- and/or the nonionic surfactant can be also carried out by using the means useful for forming the non-water-absorbing and hardly water-soluble powder(s). When the physiologically active substance is a peptidic substance, preparation of powder can be carried out with maintaining physiological activity thereof by lyophilizing an aqueous mixed solution of the peptidic physiologically active substance and polyethylene glycol, and adding an organic solvent which does not dissolve the polypeptide but dissolves polyethylene glycol to the resulting solid material (Japanese Unexamined Patent Publication No. Hei. 11-302156), or by adding an organic solvent which does not dissolve a peptide and is water-miscible to a frozen product of an aqueous mixed solution containing a peptidic physiologically active substance and a phase-separation inducing agent (WO 02/30449), and recovering powder of the peptidic physiologically active substance from the formed suspension.

Also, the physiologically active substance and/or the mucolytic agent- and/or the nonionic surfactant can be used by fixing on the surface of the non-water-absorbing and hardly water-soluble powder(s) to prepare a powdery preparation for nasal administration of the present invention, and can be used in this form.

For example, the physiologically active substance and/or the mucolytic agent- and/or the nonionic surfactant is/are dissolved in an aqueous solvent (for example, water, aqueous ethanol, aqueous acetone, aqueous methanol, aqueous acetonitrile), the solution is added to the non-water-absorbing and hardly water-soluble powder(s), the mixture is dried by the method such as drying under reduced pressure, drying at normal temperature, lyophilization, etc., and if necessary, the resulting product is sieved, to fix the physiologically active substance and/or the mucolytic agent- and/or the nonionic surfactant on the surface of the non-water-absorbing and hardly water-soluble powder(s).

Alternatively, an aqueous solvent (for example, water, aqueous ethanol, aqueous acetone, aqueous methanol, aqueous acetonitrile) is added to a mixture of the powder of a non-water-absorbing and hardly water-soluble substance, the physiologically active substance and/or the mucolytic agent- and/or the nonionic surfactant. The resulting mixture is kneaded, dried, again pulverized and sieved to have a desired particle diameter, whereby the physiologically active substance and/or the mucolytic agent- and/or the nonionic surfactant is/are fixed on the non-water-absorbing and hardly water-soluble powder(s) to prepare the powdery preparation for nasal administration of the present invention.

Incidentally, the powdery preparation for nasal administration of the present invention is administered in a dry state, and no solvent is added to the preparation. However, when the other powder solid components do not exert any adverse effects on the nasal mucous membrane, and do not inhibit nasal absorption, other additional components may be added in a small amount to increase the total amount of the preparation so that an administration (spraying/inhalation) dose of the physiologically active substance per one time becomes constant and the stability of the physiologically active substance is improved.

As such a component to be added in a small amount may be mentioned, for example, a lubricant [talc, stearic acid and its salt (sodium salt, calcium salt), Carplex, etc.], a binder (starch, dextrin, etc.), a pH adjusting agent (citric acid, glycine, etc.), a preserver (ascorbic acid, etc.), an antiseptic agent (paraoxybenzoates, benzalkonium chloride, phenol, chlorobutanol, etc.), odor masking agent (menthol, citrus flavoring, etc.).

The powdery preparation for nasal administration of the present invention can be administered into nasal cavity by spraying, and a predetermined amount of the powdery preparation for nasal administration can be sprayed into the nasal cavity with air or a gas (air, nitrogen gas, argon gas, carbon dioxide gas, substitute flon gas, etc.) which does not cause any adverse effect to human body.

As a method of spraying, any conventionally used devices for nasal administration can be used, and for example, there may be considered a method in which the powdery preparation for nasal administration of the present invention is filled in a device for pressure administration with a predetermined dose spraying system, and is sprayed into nasal cavity with each predetermined dose, a method in which the powdery preparation for nasal administration of the present invention is filled in a capsule, etc. in a predetermined amount, and when necessity arises, the capsule, etc. is mounted as such on the device for pressure administration and is made by perforation, etc. in a state wherein the powdery preparation for nasal administration can be sprayed, and the powdery preparation is sprayed with air or a gas which does not exert any adverse effects on the human body into nasal cavity, and the like.

Further, a spraying speed of air or a gas which does not exert any adverse effects on the human body at the time of spraying is preferably controlled so that almost all the constitutional components of the powdery preparation for nasal administration reaches mucous membranes of concha nasalis superior, concha nasalis media, concha nasalis inferior which have the most efficient absorption ratio among the mucous membranes of the nasal cavity, and in addition to the spraying speed of the gas, the powdery preparation for nasal administration is sprayed synchronized with the inhalation of air through the nose of the patient to be nasally administered to give more efficient delivery thereof to the absorption site.

Moreover, the powdery preparation for nasal administration of the present invention can be nasally absorbed only by inhalation without spraying it into the nasal cavity. The powdery preparation for nasal administration of the present invention is filled in a blister pack, etc. with a predetermined dose, and when necessity arises, it is mounted as such on a inhalation device, and is converted to a state that the powdery preparation for nasal administration can be taken out by pressure, etc., and the preparation is subjected to inhalation whereby the powdery preparation for nasal administration can reach the nasal cavity.

Concomitantly, the powdery preparation for nasal administration of the present invention can be used for administration through lung, administration through pharynx mucous membrane, etc., or may be administered to a patient by using a conventionally used administration device (spraying/inhalation device for administration through lung, spraying device for administration through pharynx mucous membrane, etc.) according to the administration method.

EXAMPLE

Next, the present invention is explained more concretely by referring to Examples, but the scope of the present invention is not limited by these.

Example 1

1.0 mg of salmon calcitonin (molecular weight: 3431.9, available from BACHEM Co., average particle diameter: 36.6 μm, hereinafter referred to as SCT), 1.5 mg of N-acetyl-L-cysteine (available from Fluka, average particle diameter: 45.8 μm, hereinafter referred to as NAC) and 27.5 mg of ethyl cellulose (available from Dow Chemical, Ethocel #10, average particle diameter: 81.4 μm, ethylation degree: 87 to 90%, hereinafter referred to as EC) were mixed well to give a powder for administration.

Example 2

1.0 mg of SCT, 1.5 mg of NAC and 27.5 mg of cellulose acetate (available from Katayama Chemical Industries Co., Ltd., average particle diameter: 88.0 μm, acetylation degree: 53 to 56%, hereinafter the same) were mixed well to give a powder for administration.

Example 3

In 0.3 ml of 30% aqueous ethanol was dissolved 10 mg of human insulin sodium salt (molecular weight: 5749.5, available from Sigma, hereinafter referred to as INS), the resulting solution was added to 90 mg of EC, and the resulting mixture was dried under reduced pressure at room temperature overnight to give a mixed powder of INS and EC. 10 mg of the thus-obtained mixed powder of INS and EC, 1.5 mg of NAC and 18.5 mg of EC were mixed well to give a powder for administration.

Example 4

In 0.3 ml of 30% aqueous ethanol was dissolved 5 mg of human parathyroid hormone 1-34 (molecular weight: 4117.8, available from BACHEM Co., hereinafter referred to as PTH), the resulting solution was added to 45 mg of EC, and the resulting mixture was dried under reduced pressure at room temperature overnight to give a mixed powder of PTH and EC. 10 mg of the thus-obtained mixed powder of PTH and EC, 1.5 mg of NAC and 18.5 mg of EC were mixed well to give a powder for administration.

Example 5

In 0.3 ml of 30% aqueous ethanol was dissolved 10 mg of SCT, the resulting solution was added to 90 mg of EC, and the resulting mixture was dried under reduced pressure at room temperature overnight to give a mixed powder of SCT and EC. 30 mg of the thus-obtained mixed powder of SCT and EC, 1.5 mg of NAC and 68.5 mg of EC were mixed well to give a powder for administration.

Example 6

In 60 g of 20% aqueous ethanol containing 0.1N-HCl was dissolved 3 g of bovine insulin (molecular weight: 5800, available from Sigma, hereinafter referred to as BINS), the resulting solution was added to 97 g of EC, and the resulting mixture was stirred and mixed by a small sized high speed mixer and dried at 50° C. for 4 hours to give a mixed powder of BINS and EC. 1.5 g of NAC was similarly dissolved in 60 g of 20% aqueous ethanol, the resulting solution was added to 98.5 g of EC, and the resulting mixture was stirred and mixed by a small sized high speed mixer and dried at 50° C. for 4 hours to give a mixed powder of NAC and EC. The thus-obtained mixed powder of BINS and EC and the mixed powder of NAC and EC were mixed well in equal amounts to give a powder for administration.

Preparation Example 1

Disposable tip (manufactured by Nichiryo Co., Ltd., for 200 μl), three-way stop-cock (manufactured by Terumo Corporation) and a 1 ml syringe (manufactured by Terumo Corporation) were connected in this order to prepare a device for nasal administration of powder.

The top portion of the disposable tip of this device was filled with administration powder, and air was fed by the syringe, whereby the administration powder was to be sprayed to nasal cavity.

Comparative Examples 1 to 2

1.0 mg of SCT, 1.5 mg of NAC and 27.5 mg of the component shown in the next Table 1 were mixed well to give comparative powders.

TABLE 1

| Comparative example No. | Components |
|---|---|
| 1 | Lactose (available from Wako Pure Chemical Industries, Ltd., sieved so that the powder consists of particles of 150 μm or less in diameter) |
| 2 | Crystalline cellulose (available from Asahi Kasei Corporation, AVICEL PH-101, sieved so that the powder consists of particles of 150 μm or less in diameter, average particle diameter: 23.2 μm, hereinafter the same) |

Comparative Example 3

In 0.05 ml of a physiological saline for injection (available from Otsuka Pharmaceutical Co., Ltd., hereinafter the same) was dissolved 1.0 mg of SCT to give a comparative solution.

Comparative Example 4

In 0.05 ml of a physiological saline for injection were dissolved 1.0 mg of SCT and 2.5 mg of NAC to give a comparative solution.

Comparative Example 5

In 0.05 ml of a physiological saline for injection was dissolved 1.0 mg of INS to give a comparative solution.

Comparative Example 6

In 0.05 ml of a physiological saline for injection was dissolved 1.0 mg of PTH to give a comparative solution.

Comparative Example 7

In 1.0 ml of a physiological saline for injection was dissolved 3.0 mg of SCT to give a comparative solution.

Comparative Example 8

In 1.0 ml of a physiological saline for injection was dissolved 3.0 mg of BINS to give a comparative solution.

Experimental Example 1

(1) Wistar male rats (9 to 11-weeks old, body weight: 190 to 260 g, available from Nippon SLC) were accustomed to the conditions of 12 hours illumination at room temperature 23 ±2° C., supplied freely with water and food for 1 week. Thereafter, rats were fasted for about 20 hours before the experiment, and after anesthesia with 50 mg/kg of pentobarbital (available from Nacalai), an operation for nasal administration was applied thereto according to the method described in International Journal of Pharmaceutics, vol. 7, pp. 317 to 325 (1981).
(2) With regard to the operated rats, a powder for administration prepared in Example 1 or 2 was administered by spraying to one of the nasal cavities of the rats of the administration group by using a device for nasal administration of powder assembled in Preparation example 1 so that a dose of SCT became 0.1 mg/rat.
On the other hand, to the comparative group, a comparative powder prepared in Comparative example 1 or 2 was administered by spraying to one of the nasal cavities of the rats so that a dose of SCT became 0.1 mg/rat. Alternatively, a comparative solution prepared in Comparative example 3 or 4 was administered to one of the nasal cavities of the rat by using micropipette so that a dose of SCT became 0.1 mg/rat.
(3) After 5, 10, 20, 30, 45, 60, 90 and 120 minutes from the administration by spraying, blood was sampled each in an amount of 0.1 ml from the jugular vein with a syringe (manufactured by Terumo Corporation, 25 G) treated by heparin (available from Mochida Pharmaceutical Co., Ltd.), and was centrifuged (12000 rpm, 3 minutes) to obtain plasma. SCT concentration in plasma was measured by using an enzyme immunoassay kit for measuring SCT (manufactured by Peninsula Laboratories).

Figure 2:
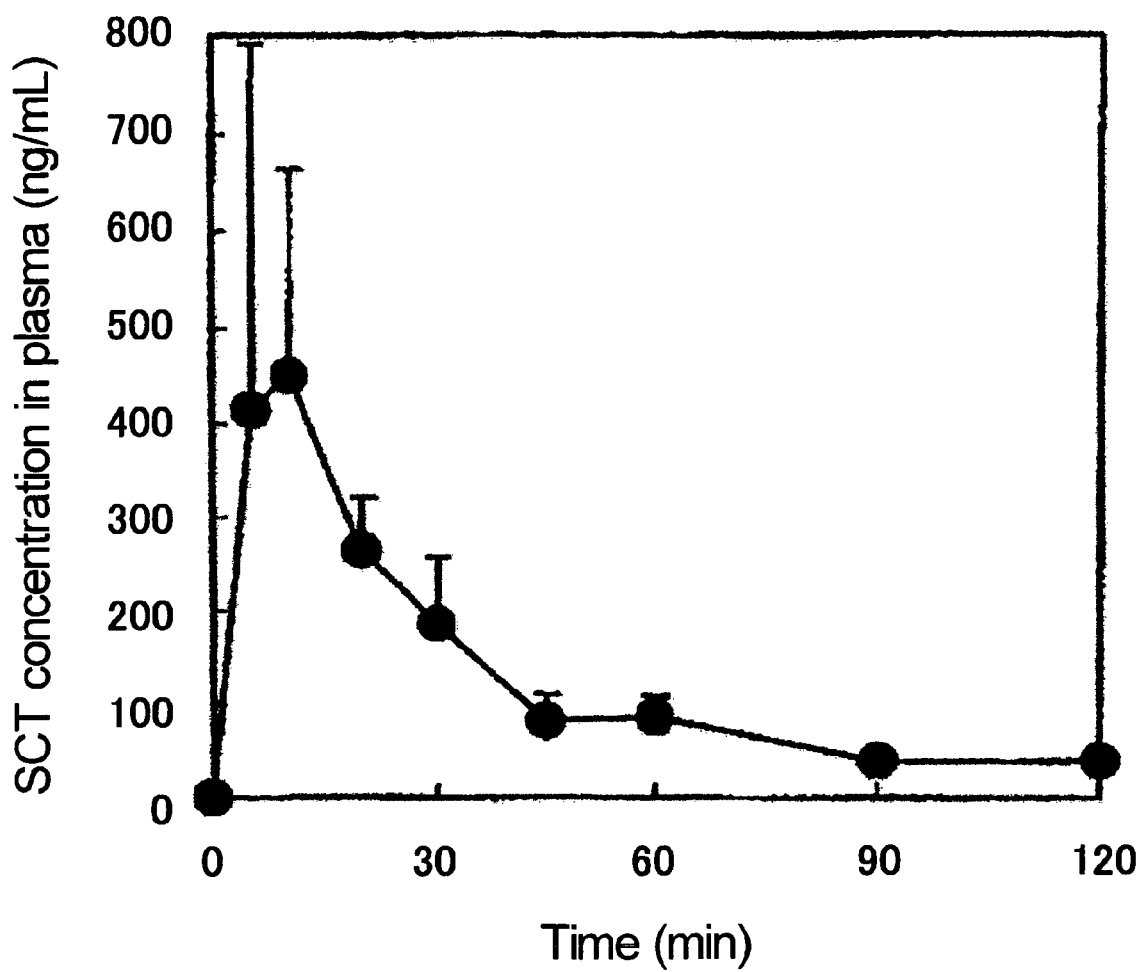
FIG. 2 shows plasma SCT concentration versus time profile when a powder for administration containing SCT, NAC and cellulose acetate is nasally administered to rats.
Figure 3:
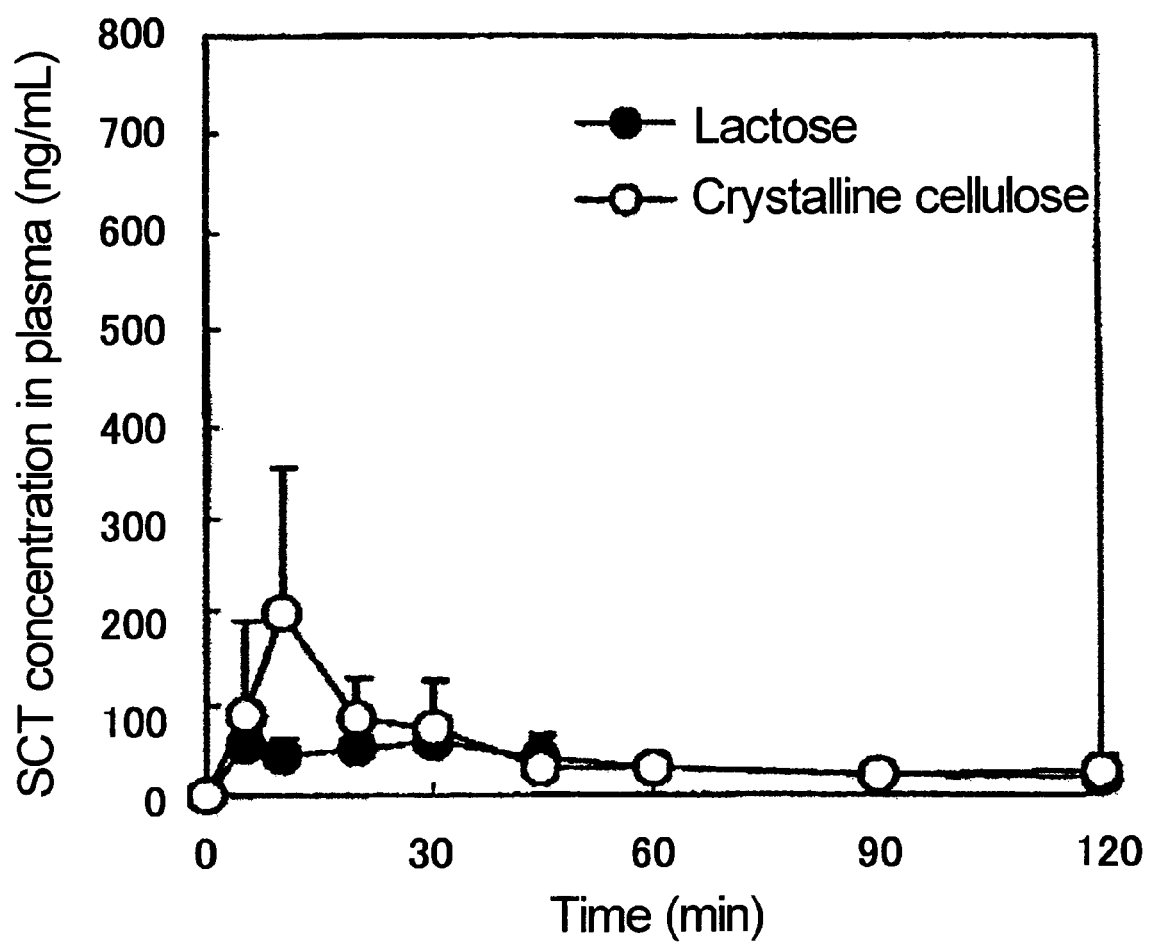
FIG. 3 shows plasma SCT concentration versus time profile when comparative powders (2 kinds) containing SCT are nasally administered to rats.
Figure 4:
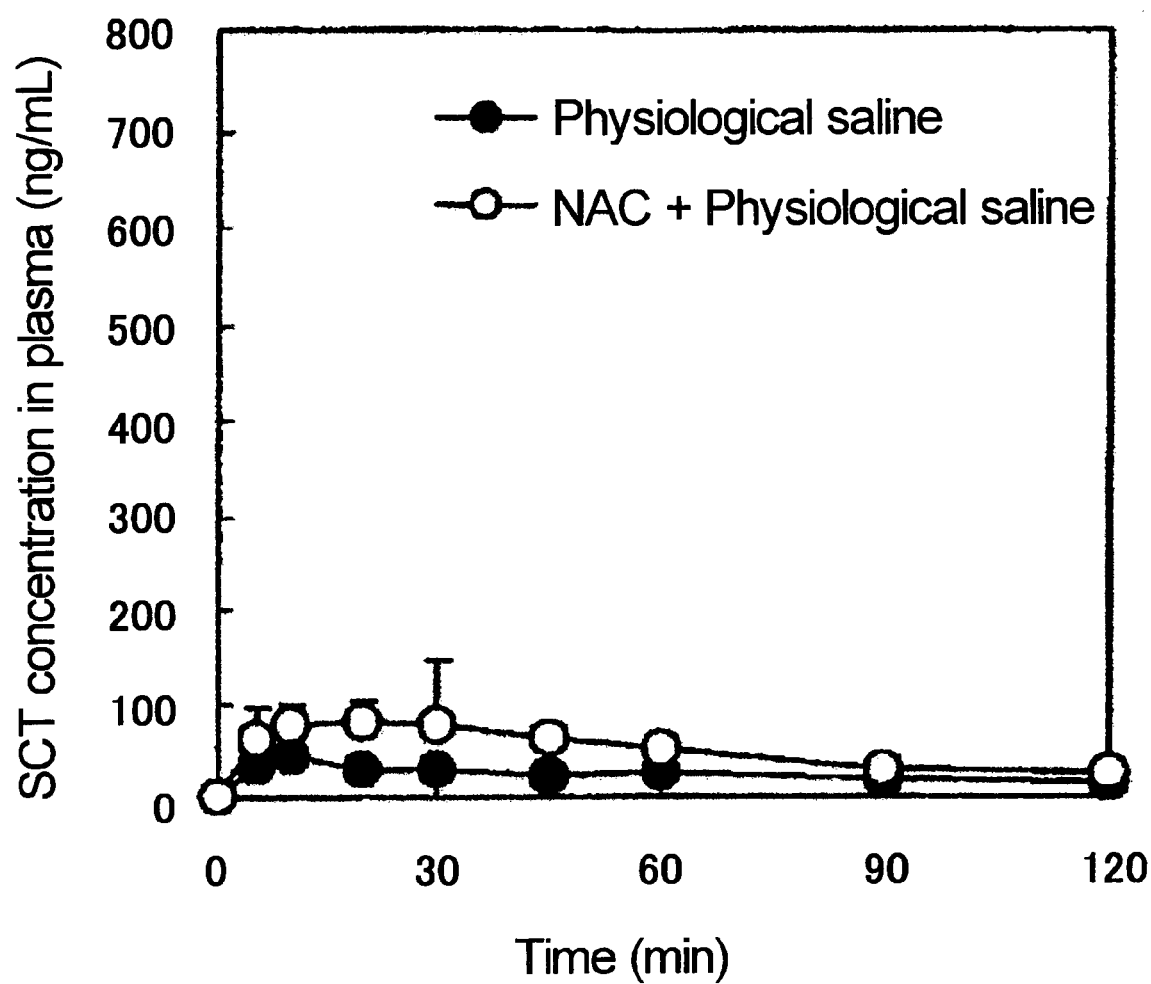
FIG. 4 shows plasma SCT concentration versus time profile when comparative solutions (2 kinds) containing SCT are nasally administered to rats.

The results of the measurement of an SCT concentration in plasma with regard to the powders for administration prepared in Examples 1 and 2 are shown in FIG. 1 and FIG. 2, respectively, and the results of the measurement of SCT concentration in plasma with regard to the comparative powders in Comparative examples 1 and 2 and the comparative solutions of Comparative examples 3 and 4 are shown in FIG. 3 and FIG. 4, respectively.

In these figures, the point indicates an average value of 3 to 5 samples, and the bar indicates a standard deviation.

Also, in these figures, AUC (Area Under Curve) was calculated according to the conventional manner, and BA (Bioavailability) by nasal administration was calculated by comparing with AUC calculated from the separate measurement results of the SCT concentration in plasma by an intravenous administration of SCT at a dose of 0.1 mg/rat (using 500 μg/ml of a physiological saline solution for injection of SCT). The results are shown in the following Table 2.

TABLE 2

| Test materials | BA (%) until 2 hours after administration |
|---|---|
| Powder for administration prepared in Example 1 | 29.7% |
| Powder for administration prepared in Example 2 | 40.7% |
| Comparative powder prepared in Comparative example 1 | 15.3% |
| Comparative powder prepared in Comparative example 2 | 10.5% |
| Comparative solution prepared in Comparative example 3 | 7.4% |
| Comparative solution prepared in Comparative example 4 | 15.7% |
| Solution (intravenous administration) | 100% |

Experimental Example 2

(1) With regard to rats obtained in Experimental example 1(1), the powder for administration prepared in Example 3 was administered by spraying to one of the nasal cavities of the rats of the administration group by using a device for nasal administration of powder assembled in Preparation example 1 so that a dose of INS became 0.1 mg/rat.

On the other hand, to the comparative group, the comparative solution prepared in Comparative example 5 was administered to one of the nasal cavities of the rat by using micropipette so that a dose of INS became 0.1 mg/rat.

(2) After 5, 10, 20, 30, 45, 60, 90 and 120 minutes from the spray administration, blood was sampled each in an amount of 0.1 ml from the jugular vein with a syringe (manufactured by Terumo Corporation, 25 G) treated by heparin (available from Mochida Pharmaceutical Co., Ltd.), and was centrifuged (12000 rpm, 3 minutes) to obtain plasma. Total insulin (INS and rat insulin) concentration in plasma was measured by using an enzyme immunoassay kit for measuring insulin (manufactured by Wako Pure Chemical Industries, Ltd.). Incidentally, INS concentrations in plasma at the respective measurement points were shown as a value by subtracting a rat insulin concentration in blood before administration from the respective measurement values.

Figure 5:
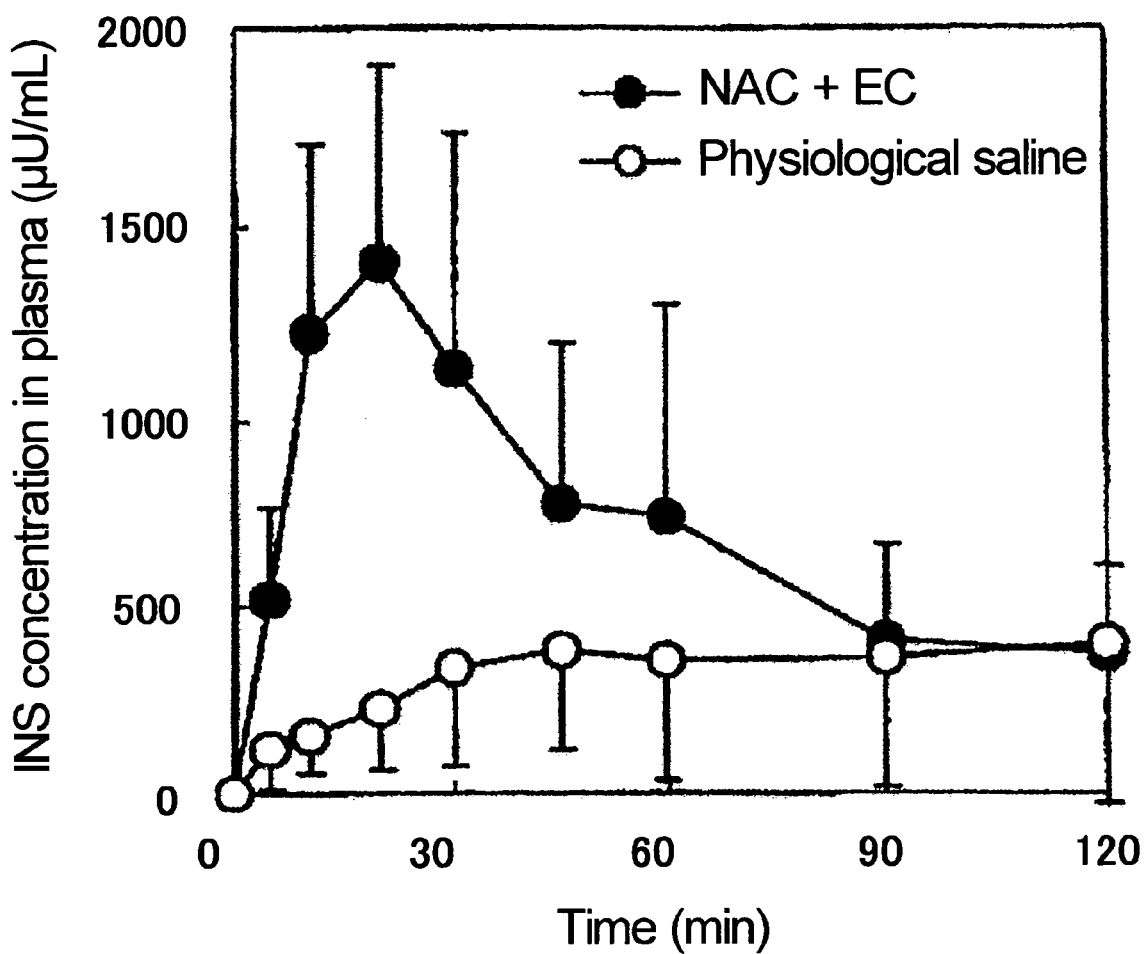
FIG. 5 shows plasma human insulin sodium salt (hereinafter referred to as INS) concentration versus time profile when a powder for administration containing INS, NAC and EC, and a comparative solution containing INS are each nasally administered to rats.

The results of the measurement of an INS concentration in plasma with regard to the powder for administration prepared in Example 3 and the comparative solution prepared in Comparative example 5 are shown in FIG. 5.

In these figures, the point indicates an average value of 5 to 7 samples, and the bar indicates a standard deviation.

Also, in these figures, AUC (Area Under Curve) was calculated according to the conventional manner, and BA (Bioavailability) by nasal administration was calculated by comparing with AUC calculated from the separate measurement results of the INS concentration in plasma by an intravenous injection of INS at a dose of 0.1 mg/rat (using 200 μg/ml of a physiological saline solution for injection of INS). The results are shown in the following Table 3.

TABLE 3

| Test materials | BA (%) until 2 hours after administration |
|---|---|
| Powder for administration prepared in Example 3 | 23.4% |
| Comparative solution prepared in Comparative example 5 | 10.5% |
| Solution (intravenous administration) | 100% |

Experimental Example 3

(1) With regard to rats obtained in Experimental example 1(1), the powder for administration prepared in Example 4 was administered by spraying to one of the nasal cavities of the rats of the administration group by using a device for nasal administration of powder assembled in Preparation example 1 so that a dose of PTH became 0.1 mg/rat.

On the other hand, to the comparative group, the comparative solution prepared in Comparative example 6 was administered to one of the nasal cavities of the rat by using micropipette so that a dose of PTH became 0.1 mg/rat.

(2) After 5, 10, 20, 30, 45, 60, 90 and 120 minutes from the spray administration, blood was sampled each in an amount of 0.1 ml from the jugular vein with a syringe (manufactured by Terumo Corporation, 25 G) treated by heparin (available from Mochida Pharmaceutical Co., Ltd.), and was centrifuged (12000 rpm, 3 minutes) to obtain plasma. PTH concentration in plasma was measured by using an enzyme immunoassay kit for measuring PTH (manufactured by Peninsula Laboratories).

Figure 6:
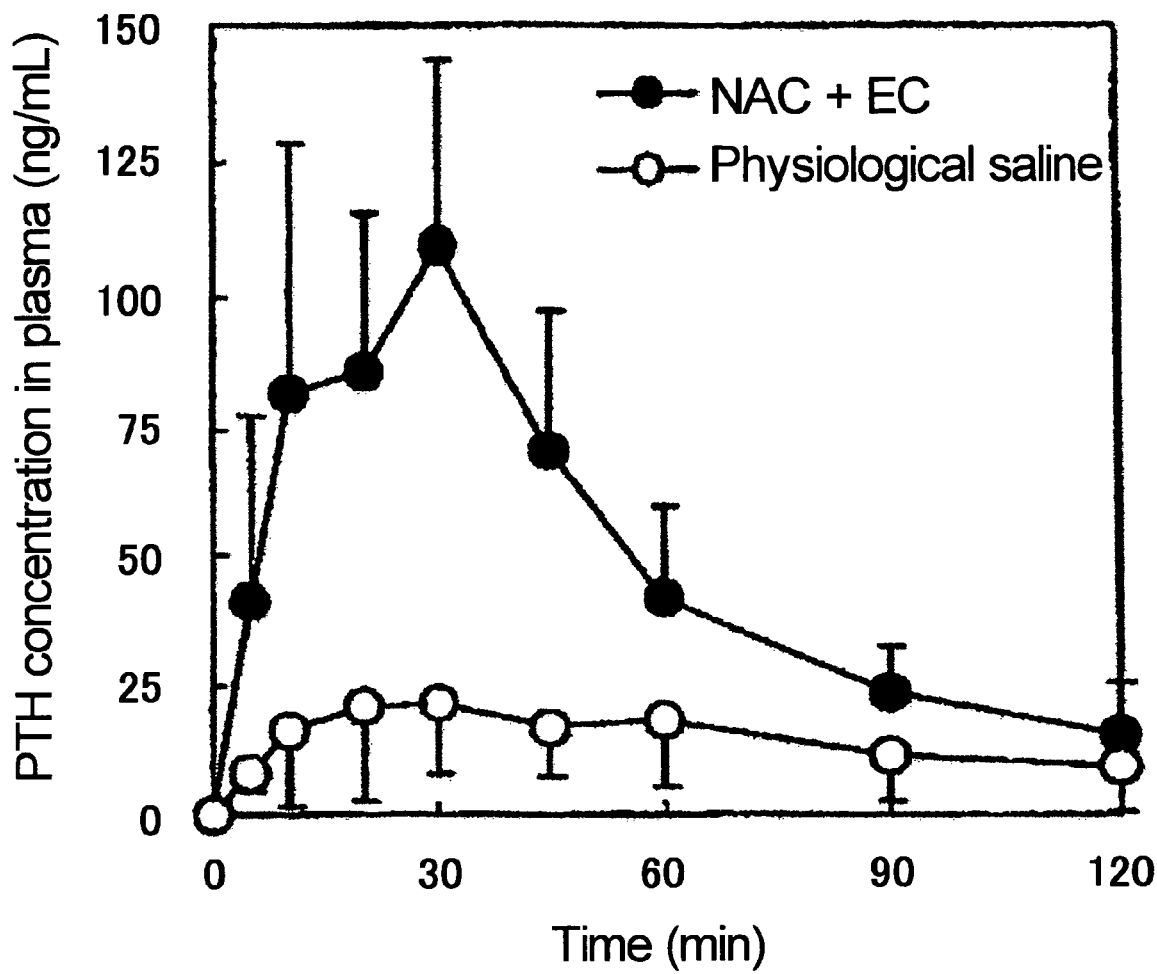
FIG. 6 shows plasma human parathyroid hormone 1-34 (hereinafter referred to as PTH) concentration versus time profile when a powder for administration containing PTH, NAC and EC, and a comparative solution containing PTH are each nasally administered to rats.

The results of the measurement of a PTH concentration in plasma with regard to the powder for administration prepared in Example 4 and the comparative solution prepared in Comparative example 6 are shown in FIG. 6.

In these figures, the point indicates an average value of 7 samples, and the bar indicates a standard deviation.

Also, in these figures, AUC (Area Under Curve) was calculated according to the conventional manner, and BA (Bioavailability) by nasal administration was calculated by comparing with AUC calculated from the separate measurement results of the PTH concentration in plasma by intravenous injection of PTH at a dose of 0.01 mg/rat (using 200 μg/ml of a physiological saline solution for injection of PTH). The results are shown in the following Table 4.

TABLE 4

| Test materials | BA (%) until 2 hours after administration |
|---|---|
| Powder for administration prepared in Example 4 | 28.2% |
| Comparative solution prepared in Comparative example 6 | 8.5% |
| Solution (intravenous administration) | 100% |

Experimental Example 4

(1) Male beagle dogs (2 year-old, body weight of 12.2 to 15.1 kg, available from Kitayama Labes Co., Ltd.) were fasted for about 20 hours before the experiment, and after anesthesia with 40 mg/kg of pentobarbital (available from Nacalai), the powder for administration prepared in Example 5 was administered by spraying to one of the nasal cavities of the dogs of the administration group by using a device for nasal administration of powder (Bi-Dose Nasal Powder device, manufactured by Pfeiffer Co.) so that a dose of SCT became 0.3 mg/dog.

On the other hand, to the comparative group, the comparative solution prepared in Comparative example 7 was administered to one of the nasal cavities of the dogs by using micropipette so that a dose of SCT became 0.3 mg/dog.

(3) After 5, 10, 20, 30, 45, 60, 90 and 120 minutes from the spray administration, blood was sampled each in an amount of 1 ml from the foreleg vein with a syringe (manufactured by Terumo Corporation, 25 G) treated by heparin (available from Mochida Pharmaceutical Co., Ltd.), and was centrifuged (12000 rpm, 3 minutes) to obtain plasma. SCT concentration in plasma was measured by using an enzyme immunoassay kit for measuring SCT (manufactured by Peninsula Laboratories).

Figure 7:
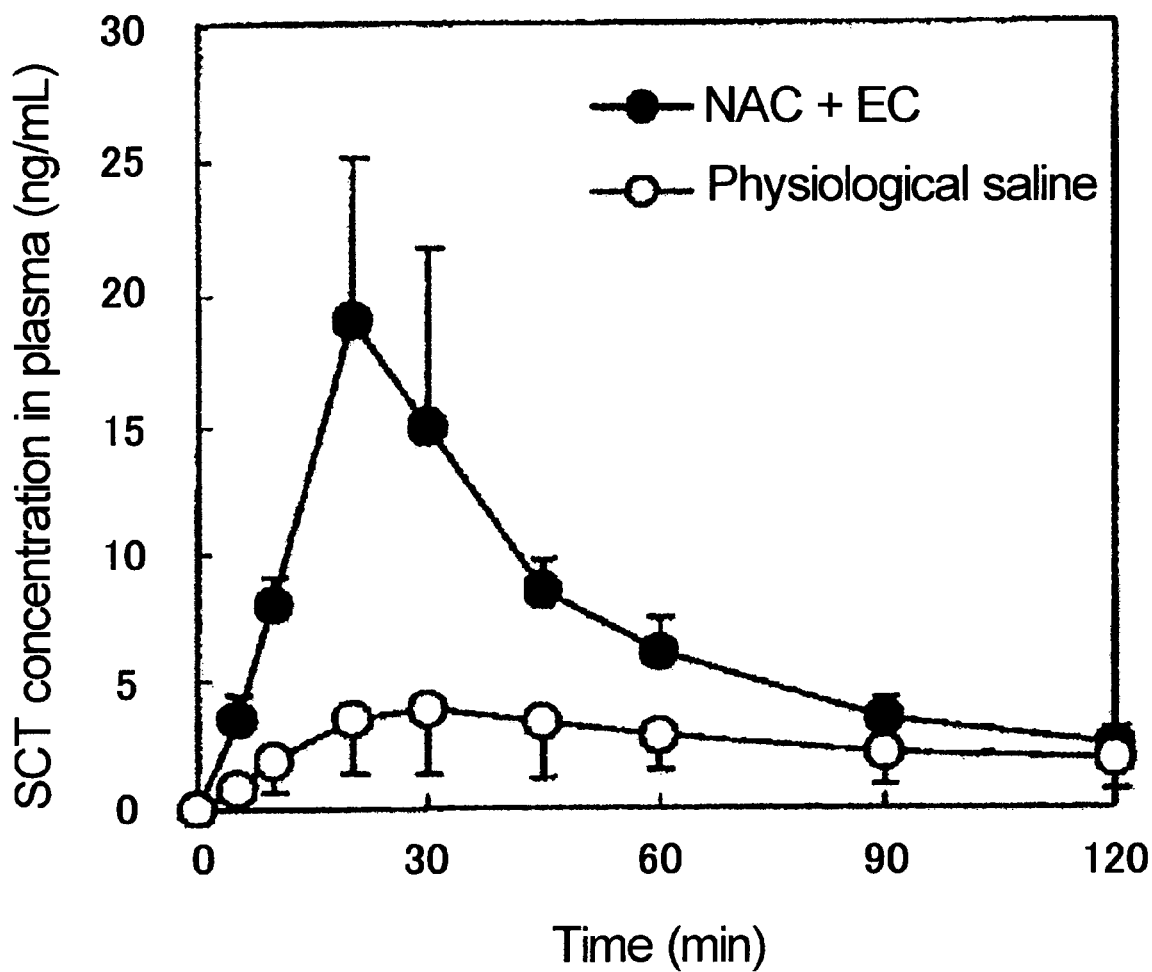
FIG. 7 shows plasma SCT concentration versus time profile when a powder for administration containing SCT, NAC and EC, and a comparative solution containing SCT are each nasally administered to dogs.

The results of the measurement of an SCT concentration in plasma with regard to the powder for administration prepared in Example 5 and the comparative solution prepared in Comparative example 7 are shown in FIG. 7.

In these figures, the point indicates an average value of 5 samples, and the bar indicates a standard deviation.

Also, in these figures, AUC (Area Under Curve) was calculated according to the conventional manner, and BA (Bioavailability) by nasal administration was calculated by comparing with AUC calculated from the measurement results of the SCT concentration in plasma by intravenous injection of SCT to dogs at a dose of 5 mg/dog (using 2.5 mg/ml of a physiological saline solution for injection of SCT). The results are shown in the following Table 5.

TABLE 5

| Test materials | BA (%) until 2 hours after administration |
|---|---|
| Powder for administration prepared in Example 5 | 23.1% |
| Comparative solution prepared in Comparative example 7 | 8.4% |
| Solution (intravenous administration) | 100% |

Experimental Example 5

(1) Male beagle dogs (3 year-old, body weight of 11.3 to 16.2 kg, available from Kitayama Labes Co., Ltd.) were fasted for about 20 hours before the experiment, and after anesthesia with 40 mg/kg of pentobarbital (available from Nacalai), the powder for administration prepared in Example 6 was administered by spraying to one of the nasal cavities of the dogs of the administration group by using a device for nasal administration of powder (Bi-Dose Nasal Powder device, manufactured by Pfeiffer Co.) so that a dose of BINS became 0.3 mg/dog.

On the other hand, to the comparative group, the comparative solution prepared in Comparative example 8 was administered to one of the nasal cavities of the dogs by using micropipette so that a dose of BINS became 0.3 mg/dog.

(2) Before spray administration and after 5, 10, 15, 20, 30, 45, 60, 90 and 120 minutes from the administration, blood was sampled each in an amount of 1 ml from the foreleg vein with-a syringe (manufactured by Terumo Corporation, 25 G) treated by heparin (available from Mochida Pharmaceutical Co., Ltd.), and was centrifuged (12000 rpm, 3 minutes) to obtain plasma. Total insulin (BINS and dog insulin) concentration in plasma was measured by using an enzyme immunoassay kit for measuring insulin (manufactured by Wako Pure Chemical Industries, Ltd.). Incidentally, BINS concentrations in plasma at the respective measurement points were shown as a value by subtracting a dog insulin concentration in blood before administration from the respective measurement values.

Figure 8:
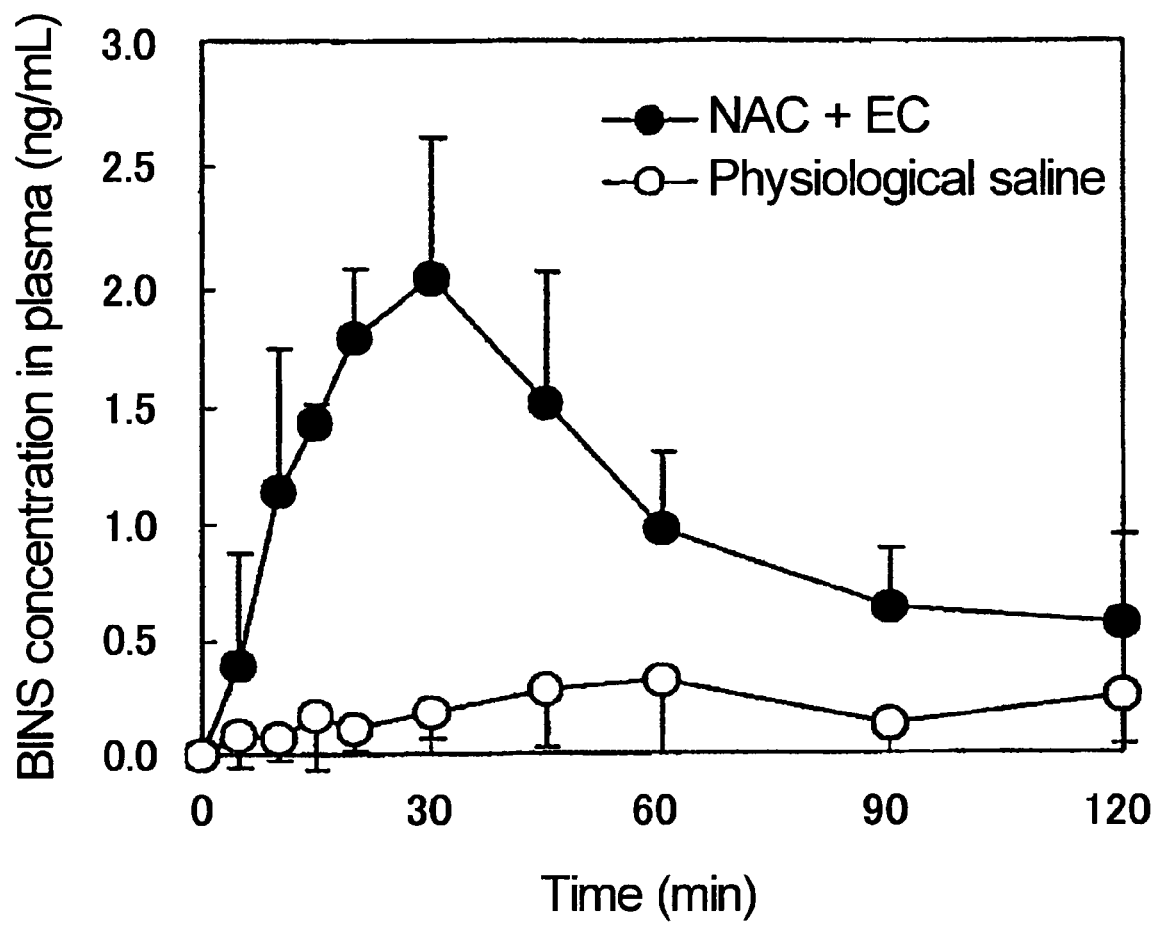
FIG. 8 shows plasma bovine insulin (hereinafter referred to as BINS) concentration versus time profile when a powder for administration containing BINS, NAC and EC, and a comparative solution containing BINS are each nasally administered to dogs.

The results of the measurement of a BINS concentration in plasma with regard to the powder for administration prepared in Example 6 and the comparative solution prepared in Comparative example 8 are shown in FIG. 8.

In these figures, the point indicates an average value of 3 or 4 samples, and the bar indicates a standard deviation.

Also, in these figures, AUC (Area Under Curve) was calculated according to the conventional manner, and BA (Bioavailability) by nasal administration was calculated by comparing with AUC calculated from the measurement results of the BINS concentration in plasma by intravenous injection of BINS at a dose of 0.3 mg/dog (using 0.3 mg/ml of a physiological saline solution for injection of BINS). The results are shown in the following Table 6.

TABLE 6

| Test materials | BA (%) until 2 hours after administration |
|---|---|
| Powder for administration prepared in Example 6 | 6.0% |
| Comparative solution prepared in Comparative example 8 | 1.3% |
| Solution (intravenous administration) | 100% |

Reference Example

According to the method described in summary collection of 16th Symposium on Particulate Preparations and Designs (1999), pp. 163 to 167, water absorption properties of EC, cellulose acetate and crystalline cellulose were investigated by the following method.

Namely, each 10 g of EC, cellulose acetate and crystalline cellulose was charged in a glass tube (inner diameter: 2.1 cm, length: 7.8 cm) for disintegration test, the bottom end of which had been capped with a filter paper. The tube was tapped with the other side down and was allowed to stand vertically in a vessel filled with pure water with a depth of 10 mm at room temperature for 1 minute.

The glass tube was taken out after 1 minute, and a distance from the bottom end thereof to the upper end portion of upward water absorption in the content in the glass tube was measured, and was estimated to be a distance of water absorption per 1 minute, which is an index of water absorption property. The results are shown in the following Table 7.

TABLE 7

| Name of component | Distance of water absorption |
|---|---|
| EC | 0.0 mm/min |
| Cellulose acetate | 0.7 mm/min |
| Crystalline cellulose | 38.0 mm/min |

Utilizability in Industry

When the powdery preparation for nasal administration of the present invention is sprayed/inhaled into nasal cavity, due to the presence of the non-water-absorbing and hardly water-soluble powder(s), the physiologically active substance and the mucolytic agent- and/or the nonionic surfactant are attached to mucous membrane of the nasal cavity and retained, and yet the non-water-absorbing and hardly water-soluble powder(s) does/do not absorb mucus of the nasal mucous membrane, so that the physiologically active substance and the mucolytic agent and/or the nonionic surfactant are dissolved in a minute amount of the mucus, whereby the physiologically active substance and the mucolytic agent- and/or the nonionic surfactant causes locally high concentration solution. In such a state, by utilizing concentration gradient of the physiologically active substance, and according to the action of the mucolytic agent- and/or the nonionic surfactant dissolved with a high concentration, absorption property itself of the nasal mucous membrane is locally improved and the physiologically active substance can reach from the nasal mucous membrane the blood vessel system existing under the membrane with good efficiency, whereby nasal absorption of the physiologically active substance can be promoted.

Also, the non-water-absorbing and hardly water-soluble powder(s) does/do not itself absorb a medicine dissolved in the nasal cavity, so that a utilization rate of the medicine is not lowered.

Moreover, the powdery preparation for nasal administration of the present invention acts on the nasal mucous membrane locally and scatteringly, so that it does not act on the whole nasal mucous membrane as in the liquid preparation for nasal administration, whereby it causes less adverse effects on the nasal mucous membrane.

The invention claimed is:

1. A powdery preparation for nasal administration which comprises
    a physiologically active substance,
    a non-water-absorbing and hardly water-soluble cellulose derivative powder(s) and
    a mucolytic cysteine derivative(s) or a combination of a mucolytic cysteine derivative(s) and a nonionic surfactant(s).

2. The powdery preparation for nasal administration according to claim 1, wherein the non-water-absorbing and hardly water-soluble cellulose derivative is a substance having a water absorption rate of 5 mm/mm or less and solubility in water at 25° C. of 100 mg/L or less.

3. The powdery preparation for nasal administration according to claim 2, wherein the non-water-absorbing and hardly water-soluble cellulose derivative is a substance having a water absorption rate of 1 mm/mm or less and solubility in water at 25° C. of 50 mg/L or less.

4. The powdery preparation for nasal administration according to claim 1, wherein the preparation contains the physiologically active substance, and the non-water-absorbing and hardly water-soluble cellulose derivative powder(s), together with a mucolytic cysteine derivative(s).

5. The powdery preparation for nasal administration according to claim 1, wherein the physiologically active substance is a hydrophilic hardly-absorbable substance.

6. The powdery preparation for nasal administration according to claim 1, wherein the physiologically active substance is a physiologically active substance with which a short on-set time produces therapeutic advantages.

7. The powdery preparation for nasal administration according to claim 1, wherein an average particle diameter of the non-water-absorbing and hardly water-soluble soluble cellulose derivative powder(s) is in the range of 5 to 200 μm, and the densities and particle diameters of the powder of the physiologically active substance and powder(s) of the mucolytic cysteine derivative(s) or the combination of the mucolytic cysteine derivative(s) and the nonionic surfactant(s) are so controlled so that the dissipation state at the time of spraying/inhalation will be the same as those of the non-water-absorbing and hardly water-soluble cellulose derivative powder(s).

8. The powdery preparation for nasal administration powder according to claim 1, wherein an average particle diameter of the non-water-absorbing and hardly water-soluble cellulose derivative powder(s) is within the range of 5 to 200 μm, and the physiologically active substance and/or the mucolytic cysteine derivative(s) or the combination of the mucolytic cysteine derivative(s) and the nonionic surfactant(s) is/are fixed on the surface of the powder.

9. The powdery preparation for nasal administration according to claim 1, wherein
    the content of the physiologically active substance is 0.1 to 80% by weight based on the whole components,
    the content of the non-water-absorbing and hardly water-soluble cellulose derivative powder(s) is 15 to 99.4% by weight based on the same, and
    the content of the mucolytic cysteine derivative(s) or the combination of the mucolytic cysteine derivative(s) and the nonionic surfactant(s) is/are 0.5 to 5% by weight based on the same.

10. The powdery preparation for nasal administration according to claim 1, wherein the cysteine derivative is at least one selected from the group consisting of N-($C_{2-5}$ alkanoyl)cysteine, S-($C_{1-4}$ alkyl)cysteine, S-($C_{2-5}$ carboxy alkyl)cysteine and glutathiones.

11. The powdery preparation for nasal administration according to claim 1, wherein the mucolytic cysteine derivative is at least one selected from the group consisting of N-acetyl-L-cysteine, S-methyl-L-cysteine, S-ethyl-L-cysteine and S-carboxymethyl-L-cysteine.

12. The powdery preparation for nasal administration according to claim 1, wherein the nonionic surfactant is at least one selected from the group consisting of a polyoxyethylene-$C_{10-14}$ alkyl ether, a polyoxyethylene-($C_{6-10}$ alkyl-phenyl) ether, a $C_{6-10}$ alkyl-glucose ether and an N-($C_{6-10}$ alkyl) carbamoyl-$C_{1-4}$ alkyl-glucose ether.

13. The powdery preparation for nasal administration according to claim 12, wherein the nonionic surfactant is a nonionic surfactant whose concentration at which 50% of red blood cells are hemolysed is 1% by weight or more.

14. The powdery preparation for nasal administration according to claim 1, wherein the physiologically active substance is a peptidic physiologically active substance or a polysaceharide physiologically active substance.

15. A powdery preparation for nasal administration which comprises a physiologically active substance, non-water-absorbing and hardly water-soluble ethyl cellulose powder or cellulose acetate powder and N-acetyl-L-cysteine.

16. The powdery preparation for nasal administration according to claim 15, wherein physiologically active substance and/or N-acetyl-L-cysteine is/are fixed on the surface of the non-water-absorbing and hardly water-soluble ethyl cellulose powder or the cellulose acetate powder.

17. The powdery preparation for nasal administration according to claim 1, wherein when said powdery preparation is sprayed or inhaled into a nasal cavity, the physiologically active substance and the mucolytic cysteine derivative(s), or the combination of the mucolytic cysteine derivative(s) and the nonionic surfactant(s) are attached to a mucous membrane of the nasal cavity and retained, and the non-water-absorbing and hardly water-soluble cellulose derivative powder(s) does not absorb mucus of the nasal mucous membrane, and consequently, the physiologically active substance and the mucolytic agent or the combination of the mucolytic cysteine derivative(s) and the nonionic surfactant(s) are dissolved in a minute amount of the mucus, whereby the physiologically active substance and the mucolytic agent or the combination of the mucolytic cysteine derivative(s) and the nonionic surfactant(s) create a locally high concentration solution.

* * * * *